(12) United States Patent
Chen et al.

(10) Patent No.: US 10,024,932 B2
(45) Date of Patent: Jul. 17, 2018

(54) MINIATURE NMR DRILL CUTTING ANALYZER AND METHODS OF USE

(71) Applicant: Halliburton Energy Services, Inc., Houston, TX (US)

(72) Inventors: Songhua Chen, Katy, TX (US); Rebecca Corina Jachmann, Kingwood, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 768 days.

(21) Appl. No.: 14/233,083

(22) PCT Filed: Mar. 1, 2013

(86) PCT No.: PCT/US2013/028673
§ 371 (c)(1),
(2) Date: Jan. 15, 2014

(87) PCT Pub. No.: WO2014/133548
PCT Pub. Date: Sep. 4, 2014

(65) Prior Publication Data
US 2014/0312901 A1    Oct. 23, 2014

(51) Int. Cl.
*G01R 33/30* (2006.01)
*G01N 24/08* (2006.01)
(Continued)

(52) U.S. Cl.
CPC ......... *G01R 33/302* (2013.01); *G01N 24/081* (2013.01); *G01R 33/383* (2013.01);
(Continued)

(58) Field of Classification Search
CPC .. G01R 33/302; G01R 33/383; G01R 33/305; G01R 33/448; G01R 33/422; G01R 33/3678; G01N 24/081
See application file for complete search history.

(56) References Cited

U.S. PATENT DOCUMENTS

| 4,654,592 A | 3/1987 | Zens |
| 6,346,813 B1* | 2/2002 | Kleinberg ............ G01N 24/081 324/303 |

(Continued)

FOREIGN PATENT DOCUMENTS

| EP | 0136536 A2 | 4/1985 |
| GB | 2341685 A | 3/2000 |

(Continued)

OTHER PUBLICATIONS

International Search Report and Written Opinion for PCT/US2013/028673 dated Nov. 25, 2013.
(Continued)

*Primary Examiner* — David M Gray
*Assistant Examiner* — Laura Roth
(74) *Attorney, Agent, or Firm* — McDermott Will & Emery LLP (57) ABSTRACT

A nuclear magnetic resonance (NMR) sample analyzer has a plurality of NMR units arrayed in a predetermined relationship to each other. Each of the NMR units includes a sample chamber having a sensitive volume for containing a sample to be analyzed; a radio frequency (RF) transmitting and receiving device proximal the sample chamber; and a magnet surrounding the RF transmitting and receiving device and sample chamber for generating a substantially uniform magnetic field within the sensitive volume and substantially no magnetic field beyond an outside wall of the magnet.

19 Claims, 7 Drawing Sheets

(51) Int. Cl.
*G01R 33/383* (2006.01)
*G01R 33/36* (2006.01)
*G01R 33/422* (2006.01)
*G01R 33/44* (2006.01)

(52) U.S. Cl.
CPC ........ *G01R 33/305* (2013.01); *G01R 33/3678* (2013.01); *G01R 33/422* (2013.01); *G01R 33/448* (2013.01)

(56) References Cited

U.S. PATENT DOCUMENTS

| | | | | |
|---|---|---|---|---|
| 6,688,390 | B2* | 2/2004 | Bolze | E21B 49/081 166/167 |
| 6,972,568 | B2 | 12/2005 | Haner et al. | |
| 7,528,600 | B2 | 5/2009 | Sen et al. | |
| 8,143,896 | B2 | 3/2012 | McDowell et al. | |
| 2004/0119471 | A1* | 6/2004 | Blanz | E21B 49/00 324/303 |
| 2007/0116602 | A1 | 5/2007 | Lee | |
| 2008/0150524 | A1 | 6/2008 | Song et al. | |
| 2009/0110242 | A1 | 4/2009 | Touati et al. | |
| 2009/0146658 | A1* | 6/2009 | McDowell | G01N 24/088 324/309 |
| 2009/0219019 | A1 | 9/2009 | Taherian et al. | |
| 2010/0207631 | A1* | 8/2010 | McDowell | G01R 33/302 324/318 |
| 2011/0091987 | A1 | 4/2011 | Weissleder et al. | |
| 2012/0049844 | A1 | 3/2012 | Leveridge et al. | |

FOREIGN PATENT DOCUMENTS

| | | |
|---|---|---|
| WO | 2006117520 A2 | 11/2006 |
| WO | 2009089007 A2 | 7/2009 |
| WO | 2009137565 A1 | 11/2009 |
| WO | 2014133548 A1 | 9/2014 |

OTHER PUBLICATIONS

Anastasios Boulis et al., "An Innovative Approach to Understanding Shale Gas Well Behavior Based on a Performance Catalogue Fingerprint," SPE Asia Pacific Oil and Gas Conference and Exhibition, SPE 160271, 2012, pp. 1-12, XP007922515.

Majidi et al., "Fingerprint of Mud Losses into Natural or Induced Fractures," SPE European Formation Damage Conference, SPE 143854, 2011, pp. 1-12, XP007922517.

International Search Report and Written Opinion for PCT/US2013/028259 dated Feb. 12, 2014.

ISSCC 2010/Session 27/ Directions in Health, Energy & RF/ IEEE International Solid-State Circuits Conference, Palm NMR and One-Chip NMR, 2010.

IEEE Journal of Solid-State Circuits (JSSC), vol. 44, No. 5, pp. 1629-1643, CMOS RF Biosensor Utilizing Nuclear Magnetic Resonance, 2009.

Official Action for Australian Patent Application No. 2013379753 dated Mar. 17, 2016.

Supplementary European Search Report received in corresponding Application No. EP13876626, dated Sep. 20, 2016.

* cited by examiner

MINIATURE NMR DRILL CUTTING ANALYZER AND METHODS OF USE

This application is a National Stage entry of and claims priority to International Application No. PCT/US2013/028673, filed on Mar. 1, 2013.

BACKGROUND

The present disclosure relates to a miniaturized nuclear magnetic resonance (NMR) sample analyzer, as for analyzing drill cutting samples, which can be operated in a laboratory or wellsite.

NMR instruments have been widely used; for example, in the energy industry, for characterizing formation rock and fluid properties in-situ, as a well logging technology, and ex-situ as a core-plug measurement technology. Low-field laboratory NMR core analyzers have sometimes been used for analysis of drill cuttings, with limited success.

Although NMR is recognized as a valuable formation evaluation technology, its widespread use has been hindered by economic concerns and technical challenges. NMR logging has only been used in a small fraction of wells because of tool operation costs and costs associated with rig time, as the signal-to-noise ratio (SNR) at reservoir temperatures and for logging measurements are considerably poorer than laboratory measurements. Limited sample availability, long turn-around time, and measurement costs prohibit many uses of NMR core plug measurements, particularly for low-margin, low-porosity, tight reservoirs such as black shale plays.

Moreover, although drill cuttings are abundant and readily available, the accuracy of information extracted from cuttings using conventional low-field NMR analyzers is not always adequate. Current NMR logging and core analyzers are all classified as low-field NMR instruments which, from a signal-to-noise ratio (SNR) consideration, is a poor choice. However, because of confined borehole spaces and the availability of power delivery downhole, only low-field logging instruments can operate in these conditions.

For laboratory core analysis, conventional NMR core analyzers are built to accommodate typical core plug sizes, ranging from 1" to 4" in diameter and 1" to 3" in length, and use permanent magnets to control manufacturing and operation costs. Although these size ranges are desirable for analysis of conventional reservoir rocks such as sandstone and limestone, their large size makes it difficult to reduce magnet size, magnetic field strength, required RF power, RF amplifier wattage, and consequently the size and cost of the entire system.

SUMMARY OF THE INVENTION

The present disclosure relates to a miniaturized nuclear magnetic resonance (NMR) sample analyzer, as for analyzing drill cutting samples, which can be operated in a laboratory or wellsite.

In some embodiments, the present disclosure provides a nuclear magnetic resonance (NMR) sample analyzer comprising a plurality of NMR units arrayed in a predetermined relationship to each other. Each of the NMR units comprises a sample chamber having a sensitive volume for containing a sample to be analyzed; a radio frequency (RF) transmitting and receiving device proximal the sample chamber; and a magnet surrounding the RF transmitting and receiving device and sample chamber for generating a substantially uniform magnetic field within the sensitive volume and substantially no magnetic field beyond an outside wall of the magnet.

In some embodiments, the present disclosure provides a nuclear magnetic resonance (NMR) sample analyzer comprising a plurality of NMR units arrayed in a predetermined relationship to each other. Each of the NMR units comprises a sample chamber having a sensitive volume for containing a sample to be analyzed; a radio frequency (RF) transmitting and receiving device proximal the sample chamber; and a magnet surrounding the RF transmitting and receiving device and sample chamber for generating a substantially uniform magnetic field within the sensitive volume and a substantially homogenous magnetic field region beyond an outside wall of the magnet.

The features and advantages of the present disclosure will be readily apparent to those skilled in the art upon a reading of the description of the embodiments that follows.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present disclosure relates to a miniaturized nuclear magnetic resonance (NMR) sample analyzer, as for analyzing drill cutting samples, which can be operated in a laboratory or wellsite. It includes a plurality of NMR measurement units arranged in a predetermined relationship to each other, such as stacked and/or arrayed, without requiring a large distance separating individual units.

Unconventional reservoir formation rocks, such as gas shales and oil shales, have unique features compared with conventional reservoir rocks, and thus require a different approach to optimize their NMR characterization techniques. Firstly, while conventional rocks typically have pore sizes in the $10^2$ to $10^1$ micron range, in black shale the typical pore size is in the $10^{-1}$ to $10^{-2}$ micron range. Since the representative sample size for black shales is 2-4 orders of magnitude smaller, cutting fragments in the millimeter size range are sufficient. Secondly, the proton NMR relaxation times for adsorbed gas or oil molecules and fluids in submicron pores are much shorter than that of fluid filled pores of conventional reservoir rocks, requiring an NMR system which has a highly homogeneous field and the capability to detect the short decaying signal. It is difficult to reduce electronics deadtime (i.e., the time between the transmitter pulse off state and the receiver window on state) in a low-field NMR system. Thus, higher magnetic field strength for operation is desirable. A small sample volume probe does not require a large magnet to achieve a magnetic field strength in the neighborhood of 1 Tesla. For example, research indicates a magnet as small as 100 g can easily achieve a half Tesla in a microcoil volume in NMR microfluidic measurements.

Most laboratory conventional reservoir rock core analysis measurements are performed in ambient conditions. Ambient conditions are suitable for analysis of conventional reservoir rocks that contain no appreciable amount of adsorbed hydrocarbon. However, in non-conventional reservoir rocks, a large amount of the gas-in-place (GIP) is in the adsorbed state, which can only be effectively probed using pressure measurements. Integrating a miniaturized pressure probe with a miniaturized transceiver, as disclosed herein, is therefore a desirable combination for low-cost NMR cutting measurements. Cutting analysis usually involves many samples, and demands fast turnaround time. Some low-field NMR measurement systems can only do one sample at a time, and may require a long time for signal averaging due to low SNR and low fields. Using the disclosed system that includes multiple miniaturized units at a higher magnetic field results in fast turnaround and low-cost mass measurements at a laboratory or wellsite.

The presently disclosed sample analyzer is particularly well-suited for analyzing drill cutting samples from unconventional reservoir formation rocks, such as gas shales and oil shales. Their submicron pore sizes result in correspondingly short proton NMR relaxation times for adsorbed gas or oil molecules and fluids in the pores, requiring an NMR system having a highly homogeneous magnet field and the capability to detect the short decaying signal.

The inventive system is miniaturized, can be operated in a laboratory or wellsite, and includes a plurality of NMR measurement units. In certain embodiments, each unit comprises a miniaturized transceiver system integrated with a pressurized micro-NMR probe, and a shaped magnet for providing a highly homogeneous magnetic field over a small "sensitive volume;" i.e., the volume to be analyzed. Using an appropriate magnet, the magnetic field is largely confined within the hole of the cylinder magnet, and the magnetic field outside the magnet is substantially zero. Thus, multiple units can be stacked without requiring a large distance separating individual units, allowing multiple samples to be analyzed at one time, thereby reducing turnaround time.

In certain embodiments, a Halbach cylinder with a length considerably exceeding the probe sensitive volume is used as the magnet. The extended length results in a reduction of edge effect. The inner radius of the cylinder is selected to be as small as possible and still house the miniature probe, while the outer radius is selected to obtain the desired field strength. The NMR probe includes a coil wrapped around a sample holder. The holder is made of materials that can withstand pressure up to 7000 psi, such as a ceramic or sapphire casing, which does not contribute to the NMR signal during the measurements.

In certain embodiments, the disclosed NMR probe is integrated with a miniaturized transceiver, including transmitter and receiver functions. The transmitter includes a pulse sequence generator, transmitter controller, power supply, and power amplifier. The receiver includes low-noise amplifier(s), a phase sensitive detector, and a transmitter/receiver isolation circuit. The transceiver is connected to an external clock such as a crystal oscillator from the input side and the back-end signal processing circuit. A computer is used for pulse program control and for processing the acquired data. In some embodiments, a gradient amplifier is included which generates current to energize a gradient coil.

To facilitate a better understanding of the present disclosure, the following examples of representative embodiments are given. In no way should the following examples be read to limit, or to define, the scope of the disclosure.

Embodiments disclosed herein include a nuclear magnetic resonance (NMR) sample analyzer comprising a plurality of NMR units arrayed in a predetermined relationship to each other. Each of the NMR units comprises a sample chamber having a sensitive volume for containing a sample to be analyzed; a radio frequency (RF) transmitting and receiving device proximal the sample chamber; and a magnet surrounding the RF transmitting and receiving device and sample chamber for generating a substantially uniform magnetic field within the sensitive volume and substantially no magnetic field beyond an outside wall of the magnet.

In a further embodiment, a nuclear magnetic resonance (NMR) sample analyzer comprising a plurality of NMR units arrayed in a predetermined relationship to each other. Each of the NMR units comprises a sample chamber having a sensitive volume for containing a sample to be analyzed; a radio frequency (RF) transmitting and receiving device proximal the sample chamber; and a magnet surrounding the RF transmitting and receiving device and sample chamber for generating a substantially uniform magnetic field within the sensitive volume and a substantially homogenous magnetic field region beyond an outside wall of the magnet.

These embodiments may have one or more of the following additional elements in any combination: Each of the NMR units comprises a transceiver operatively connected to the RF transmitting and receiving device for inducing and measuring NMR within the sensitive volume.

The transceiver may be integrated with the magnet, RF transmitting and receiving device, and sample chamber.

The NMR sample analyzer may have a single transmitter operatively connected to the RF transmitting and receiving devices of the NMR units for inducing NMR within the sensitive volumes of all the NMR units, and each of the NMR units may include a separate receiver operatively connected to the RF transmitting and receiving device for measuring the induced NMR within the sensitive volume.

In some embodiments, the NMR units may be arrayed stacked in an axial direction. In some embodiments, the NMR units may be arrayed in a plurality of stacks, each stack comprising a plurality of axially-aligned NMR units. In some embodiments, the NMR units may be arrayed in a plurality of stacks, each stack comprising a plurality of axially-aligned NMR units, and the stacks may be arranged parallel to each other.

In some embodiments, the NMR sample analyzer has an electrical shield between each of the NMR units. In some embodiments, the NMR sample analyzer has an electrical shield between each of the NMR units, and the electrical shield comprises copper. In some embodiments, the NMR sample analyzer has magnetic field permeable materials outside the cylindrical surface of the magnet to shape the magnetic field or shape a radio frequency (RF) field.

In some embodiments, the sample chamber may be for withstanding a pressure of ambient to 7000 psi. In some embodiments, the sample chamber is for withstanding a pressure of ambient to 7000 psi, and the sample chamber comprises a pressure relief valve. In some embodiments, the sample chamber is for withstanding a pressure of ambient to 7000 psi, and for withstanding a temperature of 0-150 degrees Centigrade. In some embodiments, the sample chamber is for withstanding a pressure of ambient to 7000 psi, and for withstanding a temperature of 0-150 degrees Centigrade, and comprises a ceramic or sapphire tube.

In some embodiments, the RF transmitting and receiving device comprises a coil surrounding the sample chamber. In some embodiments, the RF transmitting and receiving device comprises a coil surrounding the sample chamber, wherein the coil comprises a transmit coil operatively connectible to a transmitter for inducing NMR in the sensitive volume, and a separate receive coil operatively connectible to a receiver for sensing the induced NMR. In some embodiments, the RF transmitting and receiving device comprises a coil surrounding the sample chamber, wherein the coil comprises a transmit coil operatively connectible to a transmitter for inducing NMR in the sensitive volume, and a plurality of separate receive coils operatively connectible to corresponding respective receivers for sensing the induced NMR.

In some embodiments, the RF transmitting and receiving device comprises a coil surrounding the sample chamber, wherein the coil comprises a plurality of transmit coils operatively connectible to a transmitter for inducing NMR in the sensitive volume, and a plurality of separate receive coils operatively connectible to a receiver for sensing the induced NMR. In some embodiments, the RF transmitting and receiving device comprises a coil surrounding the sample chamber, wherein the coil comprises two perpendicular coils operatively connectible to a transmitter for inducing NMR in the sensitive volume by transmitting simultaneously with a 90 degree phase separation. In some embodiments, the RF transmitting and receiving device comprises a coil surrounding the sample chamber, wherein the coil comprises two perpendicular coils operatively connectible to a transmitter for inducing NMR in the sensitive volume by transmitting simultaneously with a 90 degree phase separation, and the two perpendicular coils are operatively connectible to a receiver or two separate receivers for sensing the induced NMR.

Each NMR unit may include a gradient coil surrounding the sample chamber, the gradient coil operatively connectible to a power source for creating a magnetic field gradient in the sensitive volume. In some embodiments, the magnet is cylindrical. In some embodiments, the magnet is cylindrical, and has a length about twice a length of the sensitive volume. In some embodiments, the magnet has a field strength of 0.5 Tesla or higher.

Figure 1:
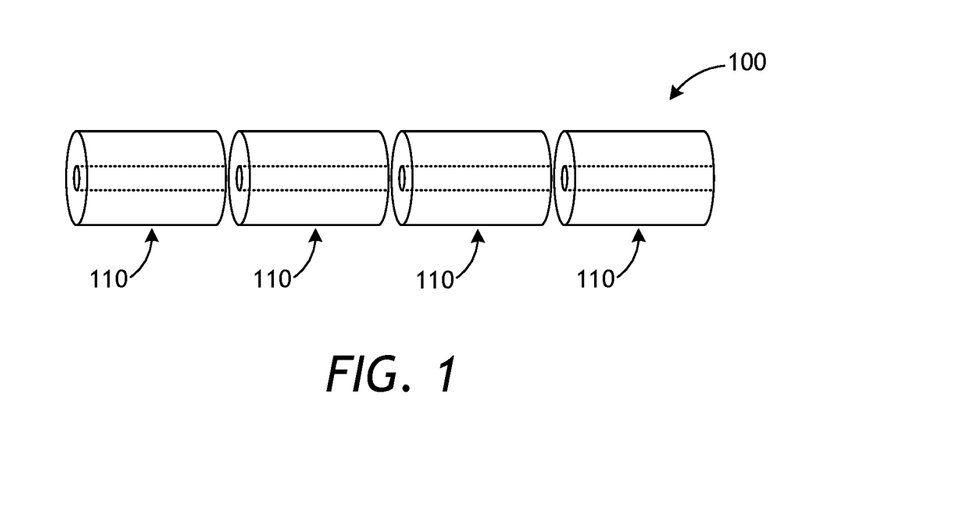
FIG. 1 is a perspective view of a NMR sample analyzer according to an embodiment of the present disclosure.
Figure 2A:
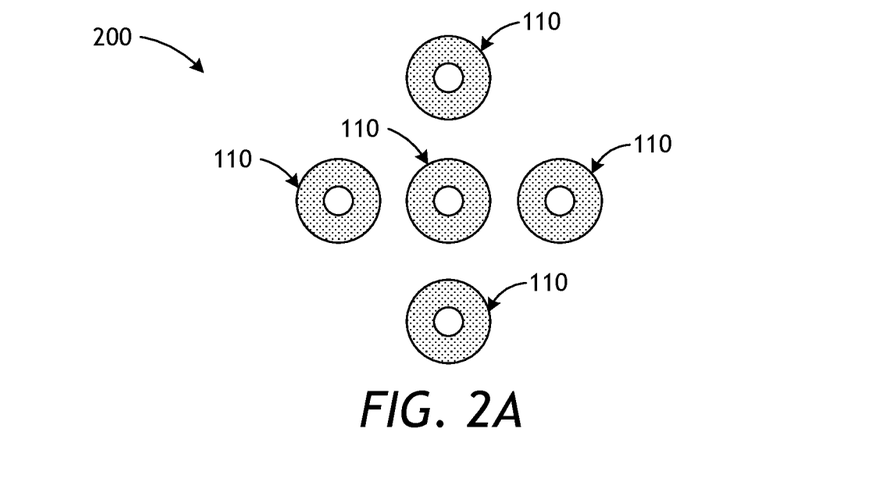
FIGS. 2A and 2B are a front and perspective view, respectively, of a NMR sample analyzer according to a further embodiment of the present disclosure.
Figure 2B:
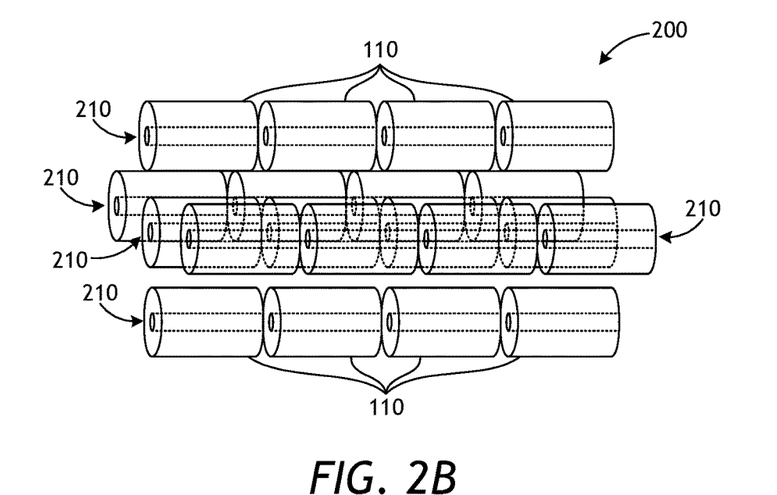
Figure 3A:
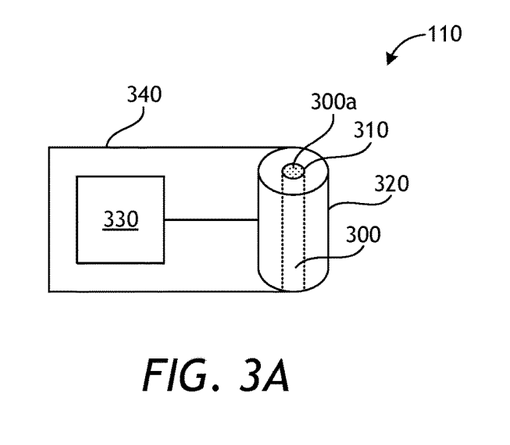
FIGS. 3A and 3B are a perspective and top view, respectively, of a NMR measurement unit according to present disclosure.
Figure 3B:
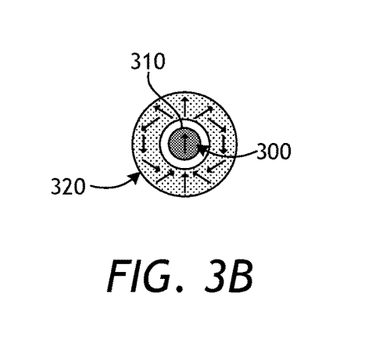

An NMR sample analyzer according to the present disclosure will now be described with reference to FIGS. 1-3B. Sample analyzer 100 may include a plurality of miniature NMR units 110 arrayed in a predetermined relationship to each other. With reference to FIGS. 3A-B, each of the NMR units 110 may include a sample chamber 300 having a sensitive volume of less than 1 cc for containing a sample to be analyzed; a radio frequency (RF) transmitting and receiving device 310 proximal the sample chamber, such as a conventional coil (also referred to in the art as an antenna) wrapped around the sample chamber or positioned adjacent the sample chamber; and a magnet 320 surrounding the RF transmitting and receiving device 310 and sample chamber 320 for generating a substantially uniform magnetic field within the sensitive volume and substantially no magnetic field beyond an outside wall of the magnet.

Each of the NMR units 110 may further include a transceiver 330 operatively connected to the RF transmitting and receiving device 310 for inducing and measuring NMR within the sensitive volume of the sample chamber 300. In certain embodiments, the transceiver 330 may be integrated with the magnet 320, RF transmitting and receiving device 310, and sample chamber 300, as on a circuit board 340.

The transceiver 330 may include both the transmitter and receiver functions, in a conventional manner. The transmitter may include a pulse sequence generator, transmitter controller, power supply, and power amplifier. The receiver may include low-noise amplifier(s), a phase sensitive detector, and a transmitter/receiver isolation circuit. The transceiver may be connected to an external clock such as a crystal oscillator from the input side and the back-end signal processing circuit. A processor may be used for pulse program control and for processing the acquired data.

Figure 4:
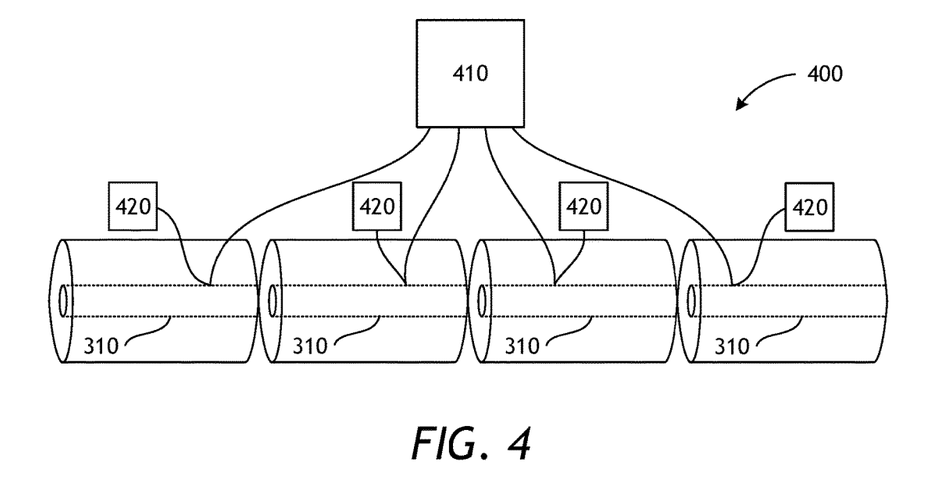
FIG. 4 is a perspective view of a NMR sample analyzer according to a still further embodiment of the present disclosure.

In certain embodiments, such as shown in FIG. 4, the NMR sample analyzer 400 may include a single transmitter 410 operatively connected to the RF transmitting and receiving devices 310 of the NMR units 110 for inducing NMR within the sensitive volumes of all the NMR units 110 in an array. Each unit 110 may include a separate receiver 420 operatively connected to the RF transmitting and receiving device 310 for measuring the induced NMR within the sensitive volume.

Figure 5A:
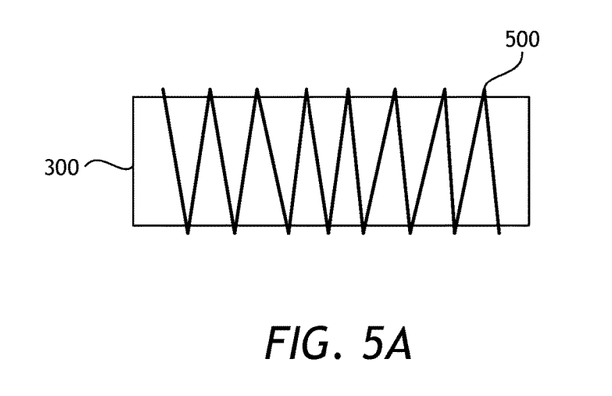
FIGS. 5A-G are side views of RF transmitting and receiving devices according to embodiments of the present disclosure.
Figure 5B:
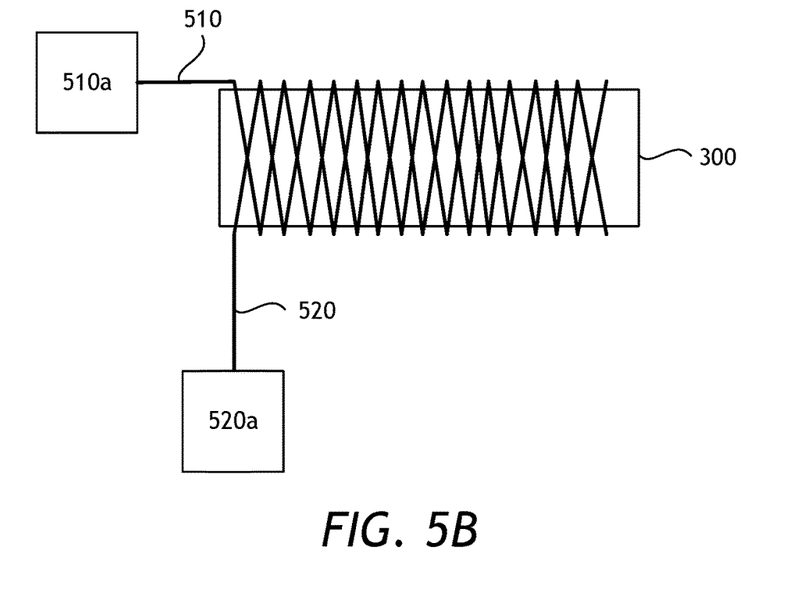

Several embodiments of the disclosed sample analyzer including different versions of the RF transmitting and receiving device 310 will now be described with reference to FIGS. 5A-G. As shown in FIG. 5A, in one embodiment an RF transmitting and receiving device may include a coil 500 surrounding the sample chamber 300. In an alternative embodiment shown in FIG. 5B, a transmit coil 510 may surround sample chamber 300, and may be operatively connectible to a conventional transmitter 510a for inducing NMR in the sensitive volume of sample chamber 300. A separate receive coil 520 may also surround sample chamber 300, and may be operatively connectible to a conventional receiver 520a for sensing the induced NMR.

Figure 5C:
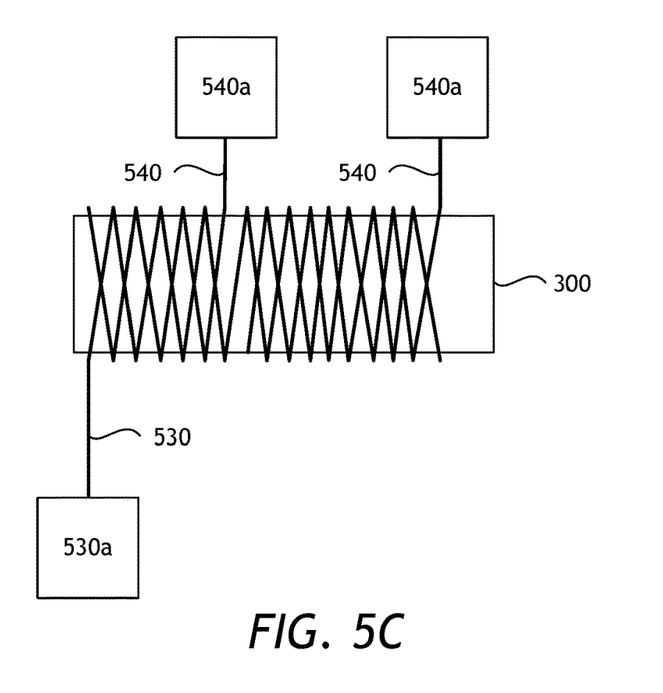
Figure 5D:
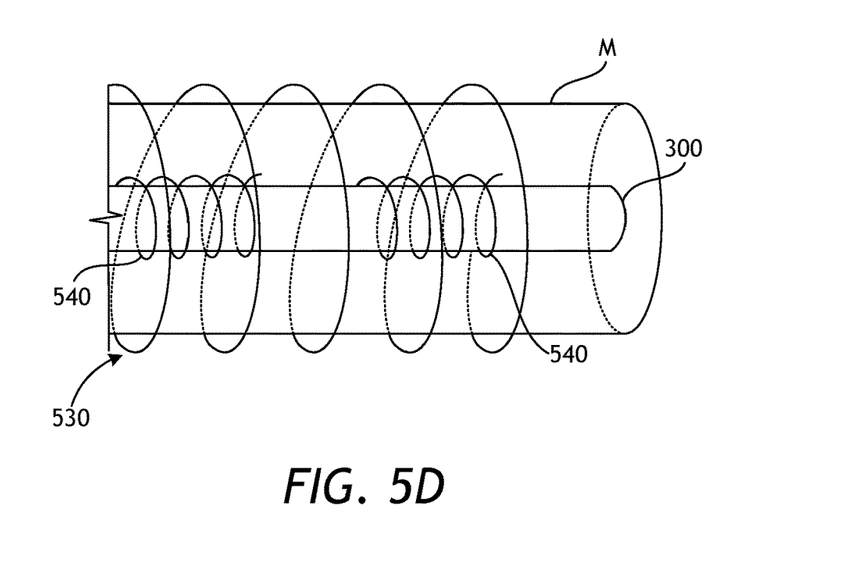

In the embodiment of FIG. 5C, a transmit coil 530 surrounds sample chamber 300 and may be operatively connectible to a conventional transmitter 530a for inducing NMR in the sensitive volume of sample chamber 300. A plurality of separate receive coils 540 also surround sample chamber 300 and are operatively connectible to corresponding respective receivers 540a for sensing the induced NMR. As shown in FIG. 5D, in certain embodiments transmit coil 530 may be outside the magnet M, while receive coils 540 may be inside the magnet M.

Figure 5E:
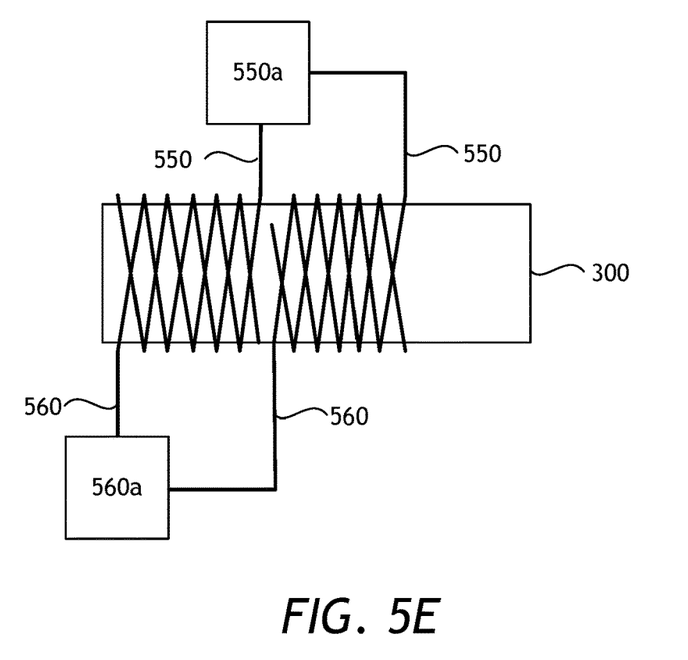

In the embodiment of FIG. 5E, a plurality of transmit coils 550 surround the sample chamber 300 and may be operatively connectible to a conventional transmitter 550a for inducing NMR in the sensitive volume of sample chamber 300. A plurality of separate receive coils 560 surrounding sample chamber 300 may be operatively connectible to a conventional receiver 560a for sensing the induced NMR.

Figure 5F:
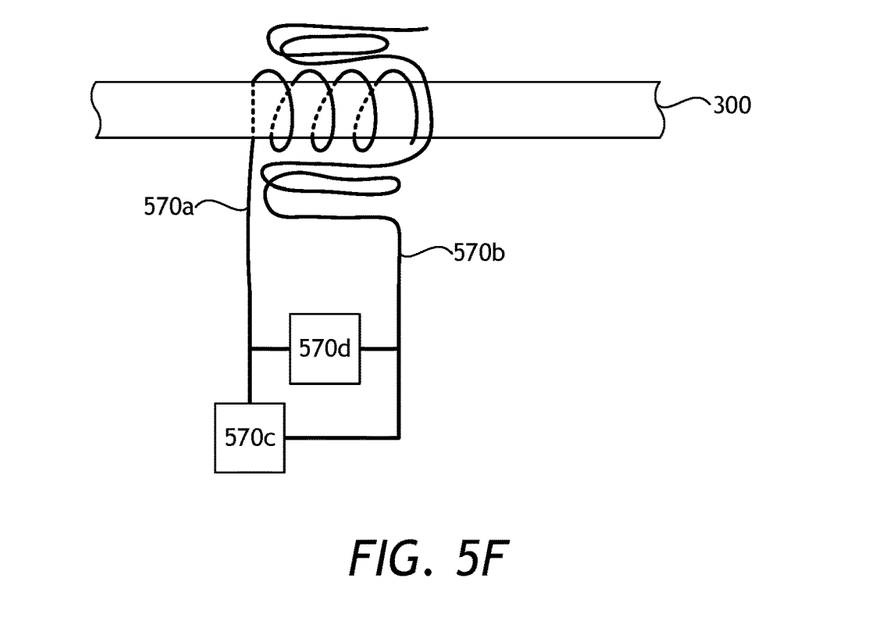

In the embodiment of FIG. 5F, two perpendicular coils 570a, 570b may be operatively connectible to a conventional transmitter 570c for inducing NMR in the sensitive volume of sample chamber 300 by transmitting simultaneously with a 90 degree phase separation. The two perpendicular coils 570a, 570b can be operatively connectible to a conventional receiver 570d (or two separate receivers 570d) for sensing the induced NMR.

Figure 5G:
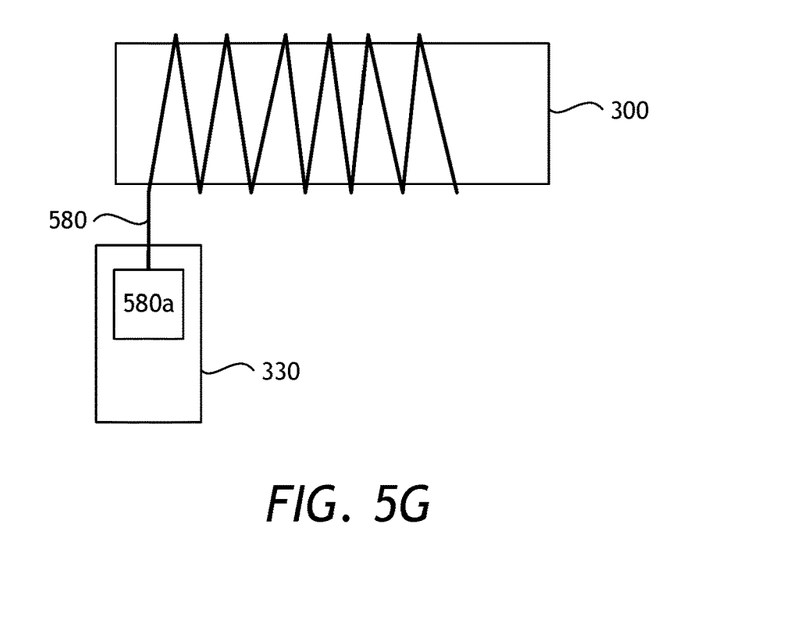

In the embodiment of FIG. 5G, each NMR unit may include a gradient coil 580 surrounding the sample chamber 300, the gradient coil 580 may be operatively connectible to a power source 580a (e.g., a gradient amplifier that is part of transceiver 330) for creating a magnetic field gradient in the sensitive volume of sample chamber 300. The gradient amplifier 580a may be controlled by a gradient-pulse-control function of transceiver 330.

In some embodiments of the disclosed sample analyzer, magnet 320 may be cylindrical in shape, and may have a length about twice a length of the sensitive volume of the sample chamber 300, to reduce the edge effect. Magnet 320 may have, for example, a field strength of 0.5 Tesla or higher; for example, about 1 Tesla. In certain embodiments, magnet 320 may be configured such that a substantially homogeneous magnetic field region results beyond an outside wall of magnet 320. A conventional Halbach cylinder magnet with a length considerably exceeding that of the probe sensitive volume can be used, for a reduction of edge effect. The inner radius of the Halbach cylinder may be selected to be as small as possible and still house the miniature probe (i.e., the sample chamber 300 and RF transmitting and receiving device 310), while the outer radius may be selected to obtain the desired field strength.

The magnet strength within the inner space of the cylinder, where the probe's sensitive volume is located, may be characterized as $H=M_r \log(r_{out}/r_{in})$, wherein $M_r$ is the remnant field of the magnetic material used to construct the Halbach cylinder, and $r_{in}$ and $r_{out}$ are the inner and outer radii of the cylinder, respectively. Inner radius $r_{in}$ is selected as small as possible to house the miniature probe, and $r_{out}$ is chosen such that the desired field strength is obtained using a selected ferrite material.

The Halbach cylinder can have a circular cross section, or a shape of any number of sides such as a square, triangle, pentagon, etc. It could instead have an oval shape, without departing from the scope of the disclosure. Any shape that can generate a uniform field inside the cylinder while cancelling the magnetic field outside the cylinder will work. Those skilled in the art of magnet crafting can easily vary the geometry and the number of segments of the magnet to achieve this purpose. Also, those skilled in the art will understand the magnet can include movable miniature magnets, or movable magnetic permeable rods, to "shim" the magnetic field as desired.

In certain embodiments, sample chamber 300 is made of materials that can withstand pressure from ambient up to 7000 psi, such as a nonmetallic ceramic or sapphire tube, which does not contribute to the NMR signal during the measurements. Such a pressurized sample chamber 300 can include a pressure relief valve 300a at its head. In further embodiments, the ceramic or sapphire sample chamber 300 is also for withstanding a temperature of 0 to 150 degrees Centigrade.

An advantage of using a magnet, such as a Halbach cylinder magnet, where the magnetic field beyond an outside wall of the magnet is substantially zero, is that two magnets placed near each other have an insignificant influence on the magnetic field inside either of them. Therefore, the NMR units 110 can be grouped in any conceivable physical manner to form the disclosed sample analyzer. For example, in FIG. 1 units 110 are arrayed stacked in an axial direction. In FIGS. 2A-B, sample analyzer 200 includes units 110 arrayed in a plurality of stacks 210 arranged parallel to each other, each stack 210 comprising a plurality of axially-aligned units 110. The actual implementation may depend on the number of units 110 desired for purposes of workflow/turnaround time, and the field uniformity requirements.

Figure 6:
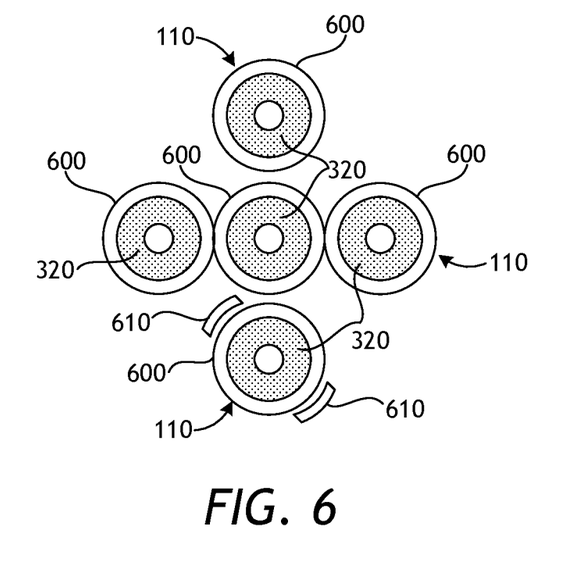
FIG. 6 is a front view of a NMR sample analyzer according to yet another embodiment of the present disclosure.

For some NMR analysis or experiments, a very uniform magnetic field may be required. In such cases, an embodiment of the disclosure features materials, such as copper, as an electrical shield between each of the units 110, to shield the antennae of each of the units 110 from each other while electrical pulses are transmitted through them. In one exemplary embodiment shown in FIG. 6, an electrical shield 600 is formed outside the cylindrical surface of each magnet 320. In certain embodiments, magnetic field permeable materials 610, such as ferrite, are arranged outside the cylindrical surface of some or all of magnets 320 to shape the magnetic field or shape the radio frequency (RF) field as desired, in a well-known manner.

Generally, in a stacked multiunit system as shown in FIGS. 2A-B, the respective units 110 in the central section will have a more uniform magnetic field sensitive volume than those in the outer sections. Therefore, experiments with different field uniformity requirements can be designed to be performed in these different locations in the stacked system. For example, the units having a higher degree of homogeneity (usually in the center) can be used to perform spectral measurements on samples, while the other units can be used to perform relaxation time measurements.

The disclosed NMR sample analyzers are suitable for NMR measurements of drill cutting samples including a FID, spin echo, inversion-recovery, saturation-recovery, or hybrid-inversion-saturation recovery for T1, and CPMG for T2 measurements. The relaxation time is used to discriminate between pore-filling fluid types, and to estimate the underlying pore sizes. Additionally, varying the interecho spacing in CPMG measurements detects the internal gradient strength which, in turn, provides estimates whether the fluid-filling pores are from a meniscus of clay particles or organic pores.

In embodiments where a gradient coil is implemented, pulse-field gradient spin-echo, and stimulated echo sequences, may be used to obtain diffusivity of the gas, condensates, and liquid phases.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The subject matter illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A nuclear magnetic resonance (NMR) sample analyzer comprising:
    a plurality of NMR units axially aligned to each other, wherein each of the plurality of NMR units comprises:
        a sample chamber having a sensitive volume for containing a sample to be analyzed;
        a radio frequency (RF) transmitting and receiving device proximal to the sample chamber;
        a separate magnet surrounding the RF transmitting and receiving device and the sample chamber for generating a substantially uniform magnetic field within the sensitive volume and substantially no magnetic field beyond an outside wall of the separate magnet; and
        a separate pressure relief valve on the sample chamber, wherein the separate pressure relief valves of the plurality of NMR units operate independently of one another.

2. The NMR sample analyzer of claim 1, wherein each of the NMR units comprises a transceiver operatively connected to the RF transmitting and receiving device for inducing and measuring NMR within the sensitive volume.

3. The NMR sample analyzer of claim 2, wherein the transceiver is integrated with the magnet, RF transmitting and receiving device, and sample chamber.

4. The NMR sample analyzer of claim 1, comprising a single transmitter operatively connected to the RF transmitting and receiving devices of the NMR units for inducing NMR within the sensitive volumes of all the NMR units, wherein each of the NMR units comprises a separate receiver operatively connected to the RF transmitting and receiving device for measuring the induced NMR within the sensitive volume.

5. The NMR sample analyzer of claim 1, wherein the NMR analyzer is further comprised of an array of a plurality of stacks, wherein each stack of the plurality of stacks comprises two or more of the plurality of NMR units axially aligned.

6. The NMR sample analyzer of claim 5, wherein the plurality of stacks are arranged parallel to each other.

7. The NMR sample analyzer of claim 1, comprising an electrical shield between each of the NMR units, wherein the sample chambers of at least two NMR units of the plurality of NMR units are separated by the electrical shield.

8. The NMR sample analyzer of claim 1, wherein the sample chamber is capable of withstanding a pressure of 7000 psi.

9. The NMR sample analyzer of claim 1, wherein the sample chamber is for withstanding a temperature of 0-150 degrees Centigrade.

10. The NMR sample analyzer of claim 1, wherein the RF transmitting and receiving device comprises a coil surrounding the sample chamber.

11. The NMR sample analyzer of claim 10, wherein the coil comprises:
    a transmit coil operatively connectible to a transmitter for inducing NMR in the sensitive volume; and
    a separate receive coil operatively connectible to a receiver for sensing the induced NMR.

12. The NMR sample analyzer of claim 10, wherein the coil comprises:
    a transmit coil operatively connectible to a transmitter for inducing NMR in the sensitive volume; and
    a plurality of separate receive coils operatively connectible to corresponding respective receivers for sensing the induced NMR.

13. The NMR sample analyzer of claim 10, wherein the coil comprises:
    a plurality of transmit coils operatively connectible to a transmitter for inducing NMR in the sensitive volume; and
    a plurality of separate receive coils operatively connectible to a receiver for sensing the induced NMR.

14. The NMR sample analyzer of claim 10, wherein the coil comprises two perpendicular coils operatively connectible to a transmitter for inducing NMR in the sensitive volume by transmitting simultaneously with a 90 degree phase separation.

15. The NMR sample analyzer of claim 14, wherein the two perpendicular coils are operatively connectible to a receiver or two separate receivers for sensing the induced NMR.

16. The NMR sample analyzer of claim 1, wherein each NMR unit comprises a gradient coil surrounding the sample chamber, the gradient coil being operatively connectible to a power source for creating a magnetic field gradient in the sensitive volume.

17. The NMR sample analyzer of claim 1, wherein the magnet is cylindrical.

18. The NMR sample analyzer of claim 17, wherein the cylindrical magnet has a length about twice a length of the sensitive volume.

19. The NMR sample analyzer of claim 1, wherein the sensitive volume of the sample chamber is operable to contain a pressurized sample.

* * * * *